United States Patent [19]

Sjoerdsma et al.

[11] 4,435,425

[45] Mar. 6, 1984

[54] FLUORINATED DIAMINOBUTANE DERIVATIVES

[75] Inventors: Albert Sjoerdsma, Cincinnati, Ohio; Philippe Bey, Strasbourg; Michel Jung, Illkirch-Graffenstaden, both of France; Fritz Gerhart, Kehl-Leutesheim, Fed. Rep. of Germany; Daniel Schirlin, Hoenhein, France

[73] Assignee: Merrell Toraude et Compagnie, Strasbourg, France

[21] Appl. No.: 373,600

[22] PCT Filed: Aug. 21, 1981

[86] PCT No.: PCT/US81/01130

§ 371 Date: Apr. 9, 1982

§ 102(e) Date: Apr. 9, 1982

[51] Int. Cl.³ ............... A61K 31/13; C07C 87/22
[52] U.S. Cl. ............... 424/325; 424/324; 424/319; 424/320; 424/330; 562/561; 562/456; 562/440; 564/510; 564/367; 564/372; 564/305; 564/215; 564/220; 564/182; 564/183; 564/184
[58] Field of Search ............... 564/510, 307, 372, 305, 564/215, 220, 182, 183, 184; 562/440, 561, 456; 424/319, 324, 325, 320, 330

[56] References Cited

U.S. PATENT DOCUMENTS

| 2,931,804 | 5/1960 | Spivack ............... | 564/510 |
| 3,975,443 | 8/1976 | Harper et al. ............... | 564/183 |
| 4,134,918 | 1/1979 | Bey ............... | 564/367 |
| 4,286,983 | 9/1981 | Gilse et al. ............... | 564/367 |

FOREIGN PATENT DOCUMENTS 2001960 2/1979 United Kingdom ............... 562/456
2083030 3/1982 United Kingdom ............... 562/561

OTHER PUBLICATIONS

Bey et al., Tit. Lett, #52, pp. 5225–6228.
Seiler et al., "Enzyme Activated Irreversible Inhibitors", pp. 55–70 (1978).

Primary Examiner—James H. Reamer
Attorney, Agent, or Firm—William J. Stein; Raymond A. McDonald; Gary D. Street

[57] ABSTRACT

Fluorinated diaminobutane compounds in vivo are inhibitors of gamma-aminobutyric acid transaminase and have the following formula:

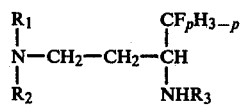

wherein:
$R_1$ represents hydrogen, $C_1$–$C_6$ alkyl, or phenyl-($C_1$–$C_4$ alkyl);
$R_2$ represents hydrogen, $C_1$–$C_6$ alkyl, phenyl-($C_1$–$C_4$ alkyl), or $R_4$, where $R_4$ is as defined below;
$R_3$ represents hydrogen, or, except when $R_2$ represents $R_4$, $R_4$, where $R_4$ is as defined below;
each $R_4$, independently, represents $C_2$–$C_5$ alkylcarbonyl, phenylcarbonyl, phenyl-($C_1$–$C_4$ alkyl) carbonyl, or an aminocarboxylic acid residue derived by removal of an hydroxy group from the carboxy moiety of an L-aminocarboxylic acid; and
p represents 1 or 2,
and pharmaceutically acceptable acid addition salts thereof.

13 Claims, No Drawings

FLUORINATED DIAMINOBUTANE DERIVATIVES

FIELD OF THE INVENTION

This invention relates to novel fluorinated diaminobutane compounds of the following general formula:

$$\begin{array}{cc} R_1 & CF_pH_{3-p} \\ | & | \\ N-CH_2-CH_2-CH \\ | & | \\ R_2 & NHR_3 \end{array}$$

wherein:
R represents hydrogen, $C_1$-$C_6$ alkyl, or phenyl-($C_1$-$C_4$ alkyl);
$R_2$ represents hydrogen, $C_1$-$C_6$ alkyl, phenyl-($C_1$-$C_4$ alkyl), or $R_4$, where $R_4$ is as defined below;
$R_3$ represents hydrogen, or, except when $R_2$ represents $R_4$, $R_4$, where $R_4$ is as defined below;
each $R_4$, independently, represents $C_2$-$C_5$ alkylcarbonyl, phenylcarbonyl, phenyl-($C_1$-$C_4$ alkyl)carbonyl, or an aminocarboxylic acid residue derived by removal of an hydroxy group from the carboxy moiety of an L-aminocarboxylic acid; and
p represents 1 or 2,
and pharmaceutically acceptable acid addition salts thereof.

The fluorinated diaminobutane derivatives in vivo are inhibitors of gamma-aminobutyric acid transaminase (GABA-T). The invention also provides pharmaceutical compositions comprising said compounds, methods of medical treatment using said compounds, and processes for preparing said compounds.

BACKGROUND OF THE INVENTION

The biotransformation of gamma-aminobutyric acid (GABA) to succinic acid semialdehyde, which is catalyzed by the enzyme GABA-transaminase (GABA-T), is the primary reaction responsible for the catabolism of GABA, an inhibitory neurotransmitter of the central nervous system. It is known that low levels of endogenous GABA are associated with seizures disorders (such as those produced by epilepsy, alcohol withdrawal, or barbiturate withdrawal), with disorders involving involuntary movement (such as Huntington's chorea, the extrapyramidal effect of drugs, for example tardive dyskinesia) and certain psychoses (such as schizophrenia and mania/depression). Blockade of the transformation of GABA to succinic acid semialdehyde, such as by irreversible inhibition of GABA-T, can elevate GABA levels in the central nervous system (CNS) and, thus provides a means for treating those disorders of the central nervous system associated with low GABA levels.

Certain compounds are known to be irreversible inhibitors of GABA-T and thereby elevate brain levels of GABA, for example fluorinated methyl gamma-aminobutyric acid and certain derivatives thereof (see U.K. Patent Specification No. 2005264A). Further, it is disclosed in U.K. Patent Specification No. 2058052A that fluorinated methyl aminopropionic acids and certain derivatives thereof are also irreversible inhibitors of GABA-T.

SUMMARY OF THE INVENTION

The compounds of the invention are represented by the following general Formula I:

$$\begin{array}{cc} R_1 & CF_pH_{3-p} \\ | & | \\ N-CH_2-CH_2-CH & \text{Formula I}\\ | & | \\ R_2 & NHR_3 \end{array}$$

wherein:
$R_1$ represents hydrogen, $C_1$-$C_6$ alkyl or phenyl-$C_1$-$C_4$ alkyl;
$R_2$ represents hydrogen, $C_1$-$C_6$ alkyl, phenyl-$C_1$-$C_4$ alkyl or $R_4$, where $R_4$ is as defined below;
$R_3$ represents hydrogen or, except when $R_2$ represents $R_4$, $R_4$, where $R_4$ is as defined below;
each $R_4$ independently represents $C_2$-$C_5$ alkyl carbonyl, phenylcarbonyl, phenyl-($C_1$-$C_4$ alkyl)carbonyl, or an aminocarboxylic acid residue derived by removal of an hydroxy group from the carboxy moiety of an L-aminocarboxylic acid; and
p represents 1 or 2.

Pharmaceutically acceptable salts of the compounds of Formula I and individual optical isomers of the compounds of Formula I are also included within the scope of the invention.

DETAILED DESCRIPTION OF THE INVENTION

In the above general Formula 1, $R_1$ and $R_2$ can be the same or different and can represent hydrogen, $C_1$-$C_6$, especially $C_1$-$C_4$, alkyl, phenyl-$C_1$-$C_4$ alkyl, preferably benzyl or phenethyl, or, in the case of $R_2$ only, $C_2$-$C_5$ alkylcarbonyl, phenylcarbonyl, phenyl-($C_1$-$C_4$ alkyl)-carbonyl, or an aminocarboxylic acid residue derived by removal of an hydroxy group from the carboxy moiety of an L-aminocarboxylic acid. It is prefered that both $R_1$ and $R_2$ represent hydrogen.

In the above general Formula I, $R_3$ represents hydrogen, or, when $R_2$ represents hydrogen, alkyl or phenalkyl, $C_2$-$C_5$ alkylcarbonyl, phenylcarbonyl, phenyl ($C_1$-$C_4$ alkyl)carbonyl, or an aminocarboxylic acid residue derived by removal of an hydroxy group from the carboxy moiety of an L-aminocarboxylic acid. Preferably, $R_3$ represents $C_2$-$C_5$ alkylcarbonyl and, especially, hydrogen.

When $R_4$ is an aminocarboxylic acid residue, it can be for example, of the formula —COCH($R_9$)NH$_2$ or —CO(CH$_2$)$_n$CH(NH$_2$)CO$_2$H wherein $R_9$ is hydrogen, $C_1$-$C_4$ alkyl, aminopropyl, aminobutyl, benzyl or p-hydroxybenzyl and n is 1 or 2. Examples of aminocarboxylic acids from which said residues are derived include glycine, alanine, leucine, lysine, isoleucine, phenylalanine, tyrosine, glutamic acid and aspartic acid.

References in this Specification, including the claims, to an alkyl group or moiety mean a straight or branched chain alkyl group or moiety and, in the case of an alkyl group or moiety having structural isomers, includes all of those isomers and mixtures thereof unless a particular isomer is specified or clearly implied by the context.

Illustrative examples of straight or branched chain alkyl groups or moieties having 1 to 4 carbon atoms are methyl, ethyl, n-propyl, iso-propyl and n-butyl.

Illustrative examples of straight or branched chain alkyl groups or moieties having 1 to 6 carbon atoms are those specified above having 1 to 4 carbon atoms and n-pentyl, neo-pentyl, n-hexyl and iso-hexyl.

In the general Formula I, p represents 1 or 2. It will be appeciated that when p represents 1 the compounds of the invention are 1-fluoro-2,4-diaminobutanes and that when p represents 2 they are 1,1-difluoro-2,4-diaminobutanes.

Illustrative examples of pharmaceutically acceptable salts of the compounds of this invention include non-toxic acid addition salts formed with inorganic acids, such as hydrochloric, hydrobromic, sulfuric, and phosphoric acid, or with organic acids such as organic carboxylic acids, for example, salicylic, maleic, malonic, tartaric, citric and ascorbic acids, and organic sulfonic acids, for example, methane sulfonic acid.

In a preferred embodiment of the invention, the compounds have the following general Formula IA.

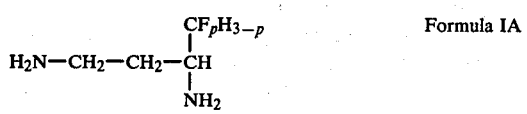

Formula IA wherein p represents 1 or 2.

Illustrative compounds of the invention are the following:
1-fluoro-2,4-diaminobutane;
1,1-difluoro-2,4-diaminobutane;
1-fluoro-2-amino-4-ethylamino-butane;
1-fluoro-2-amino-4-diethylamino-butane;
1,1-difluoro-2-(1-oxopropylamino)-4-amino-butane;
N-(1-fluoro-4-amino-2-butyl)butyramide;
N-(1,1-difluoro-4-amino-2-butyl)-2-aminoacetamide;
1,1-difluoro-2-amino-4-benzylamino-butane;
1-fluoro-2-benzoylamino-4-amino-butane; and
1,1-difluoro-2,4-di(phenylpropionylamino)-butane;

The compounds of Formula I in vivo produce irreversible inhibition of GABA-T and can elevate GABA levels significantly in the CNS when administered orally or parenterally to warm blooded animals. Thus, the compounds of Formula I are useful for treating disorders in warm blooded animals associated with low levels of GABA in the CNS. For example, the compounds of Formula I are useful as anti-convulsants for the control of seizures involved in epilepsy (grand mal and petit mal), alcohol withdrawal, and barbiturate withdrawal. The anti-convulsant activity of the compounds can be demonstrated by means of standard test procedures in laboratory animals against experimentally-induced seizures. For example, the compounds of Formula I protect mice against clonic seizures induced by bicuculline, when tested according to the procedure of W. Buckett (*Br. J. Pharm.*, 68, 177 (1980)) and *Journal of Pharmacological Methods*, 5, 35 (1981)). The compounds can also protect mice and rats against seizures induced by metrazol (clonic and tonic), maximal electroshock (tonic), and 3-mercaptopropionic acid (clonic and tonic).

It should be recognized that certain compounds of Formula I have shown toxic effects involving convulsions and weight loss ending eventually in death, when administered to mice at certain dosage levels (by single or chronic dosages). However, a significant and physiologically useful increase in GABA levels can be demonstrated experimentally in mice at chronic dosages where no lethal toxicity is observed. The dose responses after chronic administration of the hydrochloride salts of 1-fluoro-2,4-diaminobutane and 1,1-difluoro-2,4-diaminobutane with respect to the elevation of brain GABA in mice and the toxicity are shown in Example 10. The ability of the above-named compounds to protect animals against clonic seizures induced by bicuculline after a single dose is shown in Example 11.

In addition to the anti-convulsant uses, the compounds of Formula I are useful for treating disorders involving unvoluntary movement (e.g. tardive dyskinesia) and/or for treating psychoses (e.g. schizophrenia and mania/depression). Moreover, the compounds of Formula I produce sedation, myorelaxation, anorexia, hypothermia, and/or antinociception when administered systemically.

The dosage of the compounds of Formula I in warm blooded animals will depend upon the particular compound employed, the severity of the condition being treated, and the mode of administration. In general, an effective dosage capable of providing physiological useful elevation of GABA levels in the CNS can be achieved in warm blooded animals at a dose of from about 0.1 mg/kg to about 2.0 mg/kg (body weight) per day administered orally or parenterally. Therapy should be initiated at lower doses, the dosage thereafter being increased in very small increments until the desired effect is achieved.

The GABA-T inhibitory activity of the compounds can be demonstrated in laboratory animals in vivo by the methods of M. Jung et al., *J. Neurochem.*, 28, 717 (1977). In human subjects, GABA-T inhibition can be measured after systemic drug administration by determining elevated GABA levels and homocarnosine levels in cerebrospinal fluid (CSF), since there is a known correlation between GABA levels in the brain and GABA levels and homocarnosine level in CSF.

The compounds of Formula I do not inhibit GABA-T in vitro. In order to produce inhibition of GABA-T in vivo the compounds of Formula I must undergo biotransformation to the corresponding β-fluoromethyl- or β-difluoromethyl-β-alanine compounds which have the Formula A shown below:

Formula A wherein p represents 1 or 2.

The compound of Formula A are inhibitors of GABA-T in vitro and in vivo and are described in UK Application Nos. 7924030 and 8002553.

The compounds of this invention can be administered in various manners to achieve the desired effect. The compounds can be administered alone or in the form of pharmaceutical preparations to the patient being treated either orally or parenterally, for example, subcutaneously, intravenously or interperitoneally. Unit doses of these compounds can contain, for example, from about 1 mg to 50 mg of the compound and may be administered, for example, from 1 to 4 times daily.

As used herein the term patient is taken to mean warm blooded animals, such as, humans and other mammals, for example, cats, dogs, rats, mice, guinea pigs, sheep, horses and bovine cows.

The term "unit dosage form" is used herein to mean a single or multiple dose form containing a quantity of the active ingredient in admixture with or otherwise in association with the diluent or carrier, said quantity being such that one or more predetermined units are normally required for a single therapeutic administration. In the case of multiple dose forms such as liquids or scored tablets, said predetermined unit will be one fraction, such as a 5 ml (teaspoon) quantity of a liquid or a half or quarter of a scored tablet, of the multiple dose form.

In the composition aspect of the invention there are provided pharmaceutical formulations in which form the active compounds of the invention will normally be utilized. Such formulations are prepared in a manner well known per se in the pharmaceutical art and usually comprise at least one active compound of the invention in admixture or otherwise in association with a pharmaceutically acceptable carrier or diluent therefor. For making these formulations the active ingredient will usually be mixed with a carrier, or diluted by a diluent, or enclosed or encapsulated in a capsule, sachet, cachet, paper or other container. A carrier or diluent may be solid, semi-solid or liquid material which serves as a vehicle, excipient or medium for the active ingredient. Suitable carriers or diluents are well known per se.

The formulations of the invention may be adapted for enteral or parenteral use and may be administered to the patient in the form of tablets, capsules, suppositories, solutions, suspensions or the like.

In the specific examples included hereinbelow illustrative examples of suitable pharmaceutical formulations are described.

Methods of preparing the compounds of Formula I will now be described. If in any of the reaction steps described an amino group of a reactant would be involved in an unwanted reaction under the relevant reactions conditions, the amino group will be protected in manner known per se by introduction of an appropriate protecting group. The protecting group will be chosen having regard to the nature of the relevant reaction and ease of removal to free the amino group. The protecting group can be selected from, for example, acyl, for example lower alkanoyl, e.g. acetyl, propionyl, trifluoroacetyl, and the like; aroyl, e.g. benzoyl, toluoyl and the like; lower alkoxycarbonyl, for example methoxycarbonyl, ethoxycarbonyl, tert-butoxycarbonyl and the like; carbobenzoxy, benzenesulfonyl and tosyl. Both amino hydrogen atoms can be substituted by a single protecting group such as, for example phthalyl. The protecting groups are introduced in manner known per se by, for example, reaction of the amine with a lower alkanoyl or aroyl chloride, anhydride, sulfonylchloride, tert-butoxycarbonyl-oxyimino-2-phenylacetonitrile (BOC-ON), or ditertbutyl dicarbonate ((BOC)$_2$O).

Removal of the protecting group after the required reaction has been completed can be carried out in manner known per se for the relevant protecting group. Usually, said removal will be by hydrolytic cleavage using a strong organic or mineral acid such as, for example, trifluoroacetic acid, hydrochloric acid and the like acids; by catalytic hydrogenation using Pd or Pt catalyst; or by hydrogen chloride gas. Solvents used will be chosen dependent upon the nature of the conditions of protecting group removal. For example, ethers such as, for example, diethylether can be used for cleavage using hydrogen chloride gas under anhydrous conditions.

The compounds of Formula I in which $R_1$, $R_2$ and $R_3$ are all hydrogen can be obtained in manner known per se from the corresponding compound of the following general Formula II.

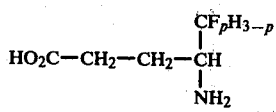

Formula II wherein: p represents 1 or 2.

The amino acids of Formula II can be converted into the compound of Formula I by the Schmidt Reaction (see, for example Organic Reactions Vol. III at page 308) in which it is treated with hydrazoic acid in the presence of a strong mineral acid such as, for example, sulfuric acid.

The amino acids of Formula II also can be converted into the corresponding compound of Formula I in which $R_1$, $R_2$ and $R_3$ are all hydrogen by the Curtius Reaction (see, for example Organic Reactions Vol. III at page 338) after protecting the amino group with, for example, an alkylcarbonyl or alkoxycarbonyl group. In the Curtius Reaction, an acid is converted to an amine via the corresponding acyl azide and isocyanate.

According to a Curtius Reaction procedure preferred for use in the present invention, the amino-protected acid reactant is treated in an aprotic solvent with diphenylphosphoryl azide in the presence of a base such as pyridine and triethylamine and subsequently treated with excess $C_1$–$C_4$ alkanol (see Yamada et al., Tet. Lett. (1973), 2343).

The 4-amino group of the resultant intermediate can be freed by hydrolytic cleavage using a strong acid such as, for example, trifluoroacetic or hydrochloric acid. Preferably, the carbamate is heated in solution in a mixture of acetic acid and hydrochloric acid. If the treatment to free the 4-amino group does not remove the protecting moiety on the 2-amino group, said moiety can be removed by appropriate treatment before or after freeing the 4-amino group.

Compounds of Formula I in which $R_1$, $R_2$ and $R_3$ are all hydrogen also can be prepared by the Hofmann Rearrangement (see, for example Organic Reactions Vol. III at page 268) of the primary amide of the acid of Formula II in which the amino group is protected with, for example, phthalimido or trifluoroacetyl. In the Hofmann Rearrangement, a primary amide is converted to an amine via the corresponding N-haloamide and isocyanate. According to a procedure preferred for use in the present invention, the amino-protected amide reactant is treated with idobenzene bis-(trifluoroacetate) in acetonitrile-water (see, for example, Radhakrishna et al, J. Org. Chem., 44 (1979) 1746/7). The amide can be obtained from the acid of Formula II in conventional manner by, for example, forming the acid chloride and treating said chloride with ammonium acetate.

The preparation of the acids of general Formula II is described in our U.K. Patent Specification No. 2055264A. Coveniently, they also can be obtained by oxidation in manner known per se of the corresponding aminoalkene of the following general Formula III whilst protecting the amino group against oxidation:

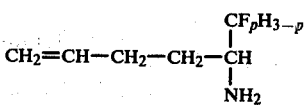

Formula III wherein: p is 1 or 2.

Preferably, the oxidation is carried out with potassium permanganate in aqueous acetic acid at room temperature overnight.

The preparation of aminoalkenes of Formula III is described hereinafter.

The compounds of Formula I in which $R_1$, $R_2$ and $R_3$ all represent hydrogen also can be obtained in manner known per se from a diamine of the following general Formula IV:

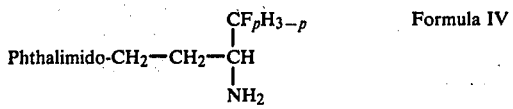

wherein p is 1 or 2, by converting the phthalimido group into a primary amino group whilst protecting the existing amino group. When p is 1, it is necessary to use a protecting group which does not leave any hydrogen atom on the amino group. Said conversion can be performed by hydrolytic cleavage using a strong mineral acid such as hydrobromic acid or hydrochloric acid or by reaction with hydrazine or methylamine. If necessary, the protecting group(s) can subsequently be removed in manner known per se.

The diamines of Formula IV can be obtained in manner known per se from an aminoacid of the following general Formula V:

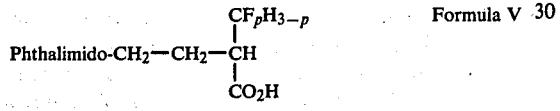

wherein p represents 1 or 2, by conversion of the acid group into a primary amino group.

The conversion of an aminoacid of Formula V into a diamine of Formula IV can be carried out by the Schimdt Reaction, Curtius Reaction or Hofmann Rearrangement, all of which have been referred to above in connection with conversion of an aminoacid of Formula II into a compound of Formula I. The reaction conditions can be such that the phthalyl group is also removed to free the amino group whereby an intermediate of Formula IV is not isolated but the reaction product is the corresponding compound of Formula I in which $R_1$, $R_2$ and $R_3$ are all hydrogen. In particular, the amide of the compound of Formula V can be treated with a iodobenzene bis(trifluoroacetate) in acetonitrile-water (see, for example, Redhakrishna et al, J. Org. Chem. 44 (1979), 1746/7.)

The aminoacids of Formula V can be obtained by decarboxylation and hydrolysis in manner known per se of an aminodiester of the following general Formula VI:

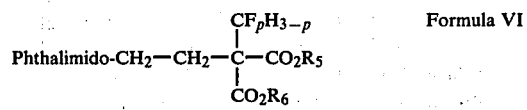

wherein:
p represents 1 or 2 and
$R_5$ and $R_6$ independently represent $C_1$-$C_4$ alkyl groups, preferably both being tert. butyl.

The conversion of an aminodiester of Formula VI into an aminoacid of Formula V can be performed by treatment with a strong acid such as, for example, hydrochloric, sulfuric acid, acetic, p-toluenesulfonic or trifluoroacetic acid.

The fluoromethylated aminodiesters of Formula VI can be obtained by mono- or di-fluoromethylation in manner known per se of an aminodiester of the following Formula VII:

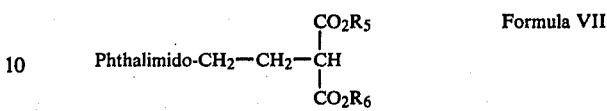

wherein: $R_5$ and $R_6$ are as defined in connection with Formula VI.

The fluoromethylation can be carried out by adding an excess of a fluoromethylating agent of the following general Formula VIII to a solution in an aprotic solvent of a carbanion derived from the aminodiester of Formula VII:

wherein:
p represents 1 or 2 and
W represents bromine, iodine or, preferably, chlorine.

The carbanion usually is obtained by treating the aminodiester of Formula VII in the aprotic solvent with a base.

The aminodiesters of Formula VII can be prepared by alkylation of a dialkyl malonate of the following general formula IX with an alkylating agent of the following general Formula X

In Formula IX, $R_5$ and $R_6$ are as defined in connection with Formula VI and in Formula X, $X^1$ is a leaving group, preferably chlorine, bromine, tosyloxy (i.e. toluene-p-sulfonyloxy), or mesyloxy (i.e. methanesulfonyloxy). The alkylation can be carried out in manner known per se in a protic or aprotic solvent using any strong base which will abstract a proton from the malonate of Formula IX.

The diamines of Formula IV also can be prepared from a corresponding hydroxyamine of Formula XI by conversion in manner known per se of the hydroxy group into a phthalimido group:

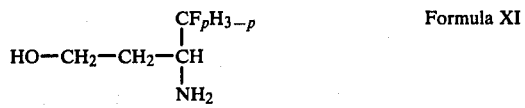

wherein p is 1 or 2.

The diamines of Formula IV can be obtained by treating the hydroxyamine of Formula XI with phthalimide in the presence of a trialkyl- or triaryl-phosphine and diethyl azodicarboxylate in an anhydrous aprotic solvent.

The amino group of the compound of Formula XI preferably is protected by phthalyl, in which case both amino groups in the resultant diphthalimido product will be simultaneously freed, or by benzyl or benzhydryl (i.e. diphenylmethyl), in which case the amino groups of the di(protected amino) product can be selectively freed. Said benzyl or benzhydryl group can be removed before or after the phthalyl group by catalytic hydrogenolysis in a protic solvent.

When the amino groups can be selectively freed, one amino group can be freed and subsequently substituted as required before freeing and if required subsequently substituting the other amino group. Substitution of the amino groups is discussed in general terms hereinafter.

The hydroxyamines of Formula XI can be obtained by reduction in manner known per se of a corresponding aminoacid or aminoester of the following general Formula XII.

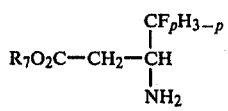

Formula XII wherein:
p is 1 or 2 and
$R_7$ represents hydrogen, $C_1$–$C_8$ alkyl or benzyl.

The amino group can be substituted by a protecting group, for example benzyl, which is not reduced under the reduction conditions used.

The reduction usually will be carried out using a reducing agent known to reduce carboxylic acid esters to alcohols such as, for example, lithium aluminium hydride or diborane in an anhydrous aprotic organic solvent.

The compounds of Formula XII can be obtained by reduction in manner known per se of a corresponding eneamine ester of the following general Formula XIII:

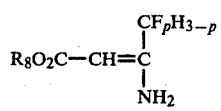

Formula XIII wherein:
p is 1 or 2
$R_8$ represents $C_1$–$C_8$ alkyl or benzyl, and, when an acid of Formula XII is required (i.e. $R_7$ is hydrogen), subsequent hydrolysis of the resultant ester of Formula XII (i.e. $R_7$ is $R_8$). The amino group can be substituted by a protecting group, for example benzyl, which is not reduced under the reduction conditions used.

The reduction can be carried out at acidic pH in a protic solvent using a borohydride salt such as sodium cyano-hydrido borate.

Said substituted eneamine esters can be prepared in manner known per se from the corresponding fluorinated aceto-acetate of the following general Formula XIV:

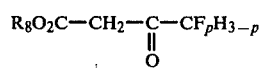

Formula XIV wherein: p and $R_8$ are as defined in connection with Formula XIII.

The fluorinated aceto-acetates can be converted into the eneamine ester by treatment with the corresponding amine in an aprotic solvent in the presence of a catalytic amount of a strong acid.

The eneamine esters also can be obtained by treatment of the corresponding fluorinated aceto-acetate of Formula XIV with an excess of ammonium acetate in anhydrous methanol.

The fluorinated aceto-acetates of Formula XIV are either known or can be prepared by analogous methods to those reported for the preparation of the known fluorinated aceto-acetates (see, for example, Bergman et al, J. Chem. Soc. (1959), 3278; McBee et al, J. Amer. Chem. Soc. 75 (1953) 3152 and Inman et al, J. Amer. Chem. Soc. 80 (1958) 6533).

The aminoacids of Formula XII in which $R_7$ represents hydrogen can be obtained in manner known per se by oxidising a corresponding aminoalkene of the following general Formula XV whilst the amino group is protected:

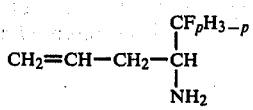

Formula XV wherein p is 1 or 2. The oxidation conditions can be as described above in connection with oxidation of an aminoalkene of Formula III to an aminoacid of Formula II.

The aminoalkenes of Formulae III and XV can be obtained from a malonic acid diester of Formula IX and an alkenyl derivative of the following general Formula XVI:

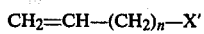

Formula XVI wherein n is 1 or 2 and X' is a leaving group, preferably chlorine, bromine, tosyloxy or mesyloxy, by an analogous reaction sequence to that described above for production of a diamine of Formula IV from compounds of Formulae IX and X. The reaction sequence is represented as follows:

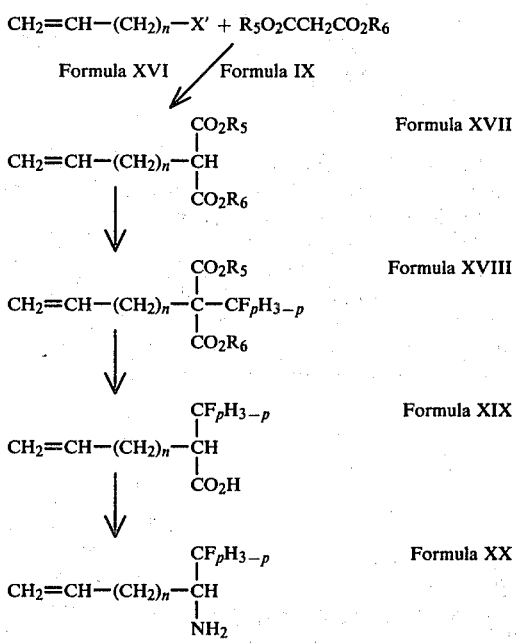

In the above sequence p is 1 or 2, $R_5$ and $R_6$ are as defined in connection with Formula IX and n and X' are as defined in connection with Formula XVI.

The compounds of Formula XV also can be obtained as described in UK Patent Specification No. 2058052A by treatment of an allyl Grignard with a fluorinated acetonitrile and subsequent reduction followed by hydrolysis of the resultant addition product.

The aminoesters of Formula XII in which $R_7$ represents $C_1$–$C_8$ alkyl or benzyl can be obtained from a malonic acid diester of Formula IX and an acetic acid derivative of the following general Formula XXI:

$$R_8O_2C\text{—}CH_2\text{—}X' \qquad \text{Formula XXI}$$

wherein $R_8$ represents $C_1$–$C_8$ alkyl or benzyl and X' represents a leaving group, preferably chlorine, bromine, tosyloxy or mesyloxy, by an analogous reaction sequence to that described above for production of a diamine of Formula IV from compounds of Formulae IX and X. The reaction sequence is represented as follows:

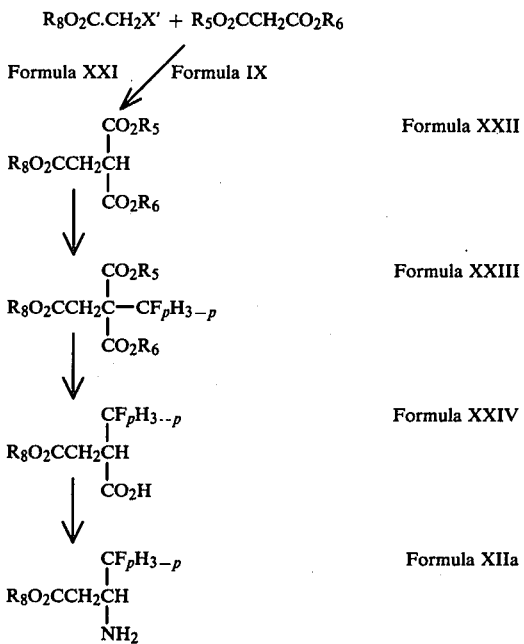

In the above sequence p is 1 or 2, $R_5$ and $R_6$ are as defined in connection with Formula IX and $R_8$ is as defined in connection with Formula XXI.

The compounds of Formula I in which $R_3$ is hydrogen and $R_1$ and $R_2$ independently represent hydrogen, $C_1$–$C_6$ alkyl or phenyl-$C_1$–$C_4$ alkyl but at least one of them is other than hydrogen can be obtained by reducing in manner known per se the corresponding aminoamide of the following general Formula XXV:

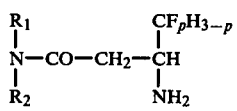 Formula XXV wherein:
p represents 1 or 2; and
$R_1$ and $R_2$ are as defined above, and The compound of Formula XXV can be used in the form of a derivative in which the amino group is substituted by one or more protecting groups which are not reduced under the reduction conditions used and said protecting group(s) subsequently removed.

The reduction can be carried out in an aprotic solvent using a reducing agent such as, for example, a boron hydride, e.g. diborane, an alkyl or alkoxy aluminium hydride, e.g. diisobutyl aluminium hydride, or lithium aluminium hydride.

The aminoamides of Formula XXV can be obtained in manner known per se from the corresponding aminoacids of the following general Formula XXVI:

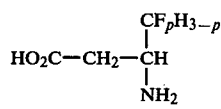 Formula XXVI wherein: p represents 1 or 2; or the corresponding amino-protected derivatives thereof.

The aminoacids of Formula XXVI can be treated with the required amine (i.e. $HNR_1R_2$) in an aprotic solvent in the presence of a coupling reagent such as, for example, dicyclohexylcarbodiimide or N-ethoxycarbonyl-2-ethoxy-1,2-dihydroquinoline.

The aminoacids of Formula XXVI are aminoacids of Formula XII in which $R_7$ represents hydrogen.

The amides of Formula I can be prepared directly or indirectly in manner known per se from the corresponding diamines of Formula I. In some, circumstances, it may be necessary to protect the non-reacting amino group prior to the reaction.

If the amide is to be formed at the 2-position (i.e. $R_3$ is to be other than hydrogen) the amino group at the 4-position (i.e. $R_1$ and $R_2$ are both hydrogen) can be protected by a phthalimido derivative, for example formed by reaction in manner known per se with a ($C_2$–$C_5$ carbalkoxy) phthalimide, e.g. carbethoxyphthalimide. When required, the phthalyl protecting group can be removed by, for example, treatment with hydrazine or methylamine.

If so desired, the phthalimido derivative can be obtained directly from a compound of Formula IV in which the primary amino group is substituted by benzyl or benzhydryl by catalytic hydrogenolysis in a protic solvent to remove the benzyl or benzhydryl group and thereby free the 2-amino group. Said catalytic hydrogenolysis has been discussed above in connection with conversion of a diamine of Formula IV to the corresponding diamine of Formula I.

If the amide is to be formed at the 4-position, the primary amino group at the 2-position can be protected by, for example, a benzoxycarbonyl group group which can be introduced by reaction in manner known per se with a benzyl haloformate, e.g. benzyl chloroformate. When required, the benzoxy group can be removed by acid hydrolysis, for example by treatment with hydrogen bromide in dioxane.

The amides can be obtained by N-acylating the corresponding compound having a primary amino group by treatment with an acid halide of the formula $R_9CO$ halogen wherein $R_9$ represents $C_1$–$C_4$ alkyl, phenyl or phenyl-$C_1$–$C_4$ alkyl, in water in the presence of a base.

In the case where the said amide has an aminocarboxylic acid residue, the amide can be prepared by N-acylation of the corresponding compound having a primary amino group with the corresponding aminocarboxylic acid or an anhydride thereof, in which acid or anhydride the amino group is protected with a suitable blocking agent such as benzoxycarbonyl or tert-butoxycarbonyl, in an anhydrous organic solvent and, when the free acid is employed, in the presence of a dehydrating agent, followed by acid or base hydrolysis.

The individual optical isomers of the compounds of Formula I wherein $R_2$ and $R_3$ are hydrogen may be separated in manner known per se by protecting the amino group distal to the fluorinated methyl group using a ($C_2$-$C_5$ alkoxycarbonyl) phthalimide in a solvent such as, for example, tetrahydrofuran, diethyl ether or $C_1$-$C_4$ alkanol, e.g. as methanol or ethanol. The protected amine derivative is then resolved using a chiral acid such as (+) or (−) binaphthylphosphoric acid by the method described by R. Viterbo et al., in Tetrahedron Letters 48, 4617–4620 (1971) and in U.S. Pat. No. 3,848,030 or (+) camphor-10-sulfonic acid. The resolved phthalimido compound is then deprotected using, for example, hydrazine or methylamine to remove the phthalimide group. The thus resolved amines may be employed to prepare the individual isomers of other compounds of the invention in the manner described hereinabove.

It is preferred however that optical resolution should be effected at the intermediate aminoacid of Formula II or Formula XII by resolving the acid or an ester thereof with a chiral acid such as binaphthyl phosphoric acid or camphor-sulfonic acid as discussed above. Alternatively, the aminoacid can be resolved by forming an amide with a chiral acid such as (−) alpha-phenylpropionic acid, separating the diasteriomers and hydrolysing the separated amides to the acids.

The compounds produced by the foregoing processes may be isolated either per se or as acid addition salts thereof.

The acid addition salts are preferably the pharmaceutically acceptable, non-toxic addition salts with suitable acids, such as those previously referred to in this Specification. Apart from pharmaceutically acceptable acid addition salts, other acid addition salts, such as for example, those with picric or oxalic acid are useful; they may serve as intermediates in the purification of the compounds of the invention or in the preparation of other, for example, pharmaceutically acceptable, acid addition salts, or are useful for identification or characterisation of the bases.

A resulting acid addition salt may be converted into the free compound according to known methods, for example, by treating it with an alkali or alkaline earth metal hydroxide or alkoxide, with an alkali or an alkaline earth metal carbonate or hydrogen carbonate, with trialkylamine; or with an anion exchange resin.

A resulting acid addition salt may also be converted into another acid addition salt according to known methods; for example, a salt with an inorganic acid may be treated with a metal salt, for example a sodium, barium or silver salt of an acid in a suitable diluent, in which a resulting inorganic salt is insoluble and is thus removed from the reaction medium. An acid addition salt may also be converted into another acid addition salt by treatment with an anion exchange preparation.

The invention is illustrated by the following non-limiting Examples. All NMR measurements are given on the delta scale (i.e. trimethylsilane=0).

EXAMPLE I

1-Fluoro-2,4-diaminobutane

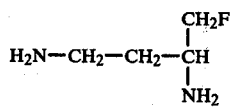

To a solution of 5-fluoro-4-amino-pentanoic acid (6.75 g, 50 mmoles) in conc. sulfuric acid (49 g, 0.5 moles) is added a solution of hydrazoic acid in chloroform (1.14 N, 44 mL) at 40° C. with vigorous stirring. Heating and stirring are continued until the end of carbon dioxide evolution (6 hours). The reaction mixture is poured into water (500 mL), heated to boiling and the sulfate is precipitated with barium chloride (105 g in 400 mL of water). After cooling to room temperature, barium sulfate is removed by filtration (celite) and the excess barium ions are precipitated by dropwise addition of 2 N sulfuric acid until no further precipitation occurs. After filtration (celite), evaporation gives a solid residue which is recrystallized from methanol/acetone to give 1-fluoro-2,4-diaminobutane dihydrochloride (2HCl, 4.7 g, 53%) as white, slightly hygroscopic crystals, Mp 135° C.

NMR ($D_2O$): 2.10 (2H, m), 3.13 (2H, m), 3.70 (1H, d of m, $J_{H-F}=22$ Hz), 4.63 (2H, d of m, $J_{H-F}=46$ Hz).

1-Fluoro-2,4-diaminobutane, dihydrochloride (1.790 g, 10 mM) is dissolved in anhydrous methanol (10 mL). Sodium methoxide (2 equiv) is added to the mixture. Evaporation of the solvent under reduced pressure affords a solid residue which is triturated with ether. Filtration of the ether solution and removal of the solvent in vacuo yield the free diamine as a colorless oil.

EXAMPLE 2

1,1-Difluoro-2,4-diaminobutane

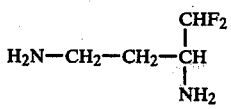

(A) Preparation of: 2-(tert.Butoxycarbonyl)5-hexenoic acid.tert.butyl ester

Di-tert.-butyl malonate (10 mM, 2.160 g) is added at room temperature under nitrogen to a suspension of sodium hydride (11 mM, 0.495 g of a 55% dispersion in oil) in tetrahydrofuran (30 ml). After stirring for 1 hour, a solution of 4-bromo-1-butene (10 mM, 1.350 g) in tetrahydrofuran (5 ml) is added dropwise over a period of 15 min; stirring is continued for 48 hours at room temperature; the mixture is then hydrolyzed and extracted twice with diethyl ether. The organic layer is dried over anhydrous magnesium sulfate and concentrated to dryness in vacuo. The diester is isolated by distillation under reduced pressure. 1.728 g (yield 64%).

Bp: 68° C./0.07 mb.

NMR (CDCl$_3$) 1.43 (s, 18H); 1.77–2.27 (m, 4H); 3.13 (t, $J_{HH}=7$ Hz, 1H); 4.77–5.20 (m, 2H); 5.42–6.13 (m, 1H).

(B) Preparation of: 2-Difluoromethyl 2-(tert.butoxycarbonyl)-5-hexenoic acid, tert-butyl ester

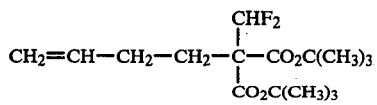

2-(tert-butoxycarbonyl)-5-hexenoic acid, tert-butylester prepared as in Step A (5 mM, 1.350 g) is added at room temperature, under nitrogen, to a suspension of sodium hydride (5.5 mM, 0.248 g of a 55% dispersion in oil) in tetrahydrofuran (20 ml). After stirring 1 hour at room temperature and 20 hours at 60° C., a stream of chlorodifluoromethane is bubbled through the anion solution. Stirring is continued for 20 hours at room temperature, and the mixture is hydrolyzed and extracted twice with ether. The organic layer is dried over anhydrous magnesium sulfate, and concentrated to dryness in vacuo. The expected product is isolated by distillation under reduced pressure. 1.000 g (yield 62%). Bp: 75° C./0.07 mb.

NMR (CDCl$_3$) 1.45 (s, 18H); 1.93–2.33 (m, 4H); 4.77–5.23 (m, 2H); 5.40–6.10 (m, 1H); 6.18 (t, $J_{HF}=54$ Hz, 1H).

(C) Preparation of: 2-Carboxy 2-difluoromethyl 5-hexenoic acid

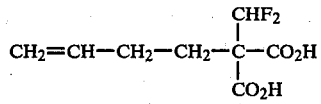

2-Difluoromethyl 2(tert-butoxycarbonyl)-5-hexenoic acid, tert-butyl ester prepared as in Step B (5 mM, 1.600 g) is dissolved in trifluoroacetic acid (10 ml) at 0° C. After stirring for 1.5 hours at room temperature, the solvent is evaporated in vacuo yielding a white solid. 1.040 g (quantitative yield). Mp: 80°–81° C.

(D) Preparation of: 2-Difluoromethyl 5-hexenoic acid

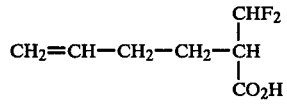

2-Carboxy 2-difluoromethyl 5-hexenoic acid, prepared as in Step C (1.040 g, 5 mM) is dissolved in glacial acetic acid (5 ml) and the mixture is heated at 110° C. for 16 hours. The solvent is evaporated in vacuo yielding a colorless oil. The acid is isolated by distillation under reduced pressure. 0.585 g (yield 71%). Bp: 67° C./0.01 mm Hg.

NMR (CDCl$_3$) 1.60–2.43 (m, 4H); 2.45–3.25 (m, 1H); 4.73–5.20 (m), 5.37–5.87 (m) and 5.90 (td, $J_{HF}=54$ Hz, $J_{HH}=6$ Hz) (4H).

(E) Preparation of: 2-Difluoromethyl 5-hexenoyl chloride

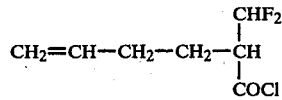

2-Difluoromethyl 5-hexenoic acid prepared as in Step D (7.940 g, 48.4 mM) is dissolved in thionyl chloride (40 ml) and the mixture is heated at reflux for 5 hours. The solvent is evaporated in vacuo yielding the required acid chloride as a yellowish oil.

NMR (CDCl$_3$) 1.70–2.50 (m, 4H); 2.87–3.78 (m, 1H); 4.77–5.24 (m), 5.37–6.00 (m) and 6.00 (td, $J_{HF}=54$ Hz, $J_{HH}=5$ Hz) (4H).

(F) Preparation of: 1,1-Difluoro-2-methoxycarbonylamino-4-pentene

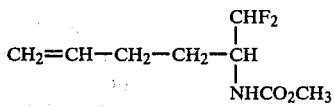

Sodium azide (3.440 g, 53 mM, 1.1 eq) in water (10 ml) is added dropwise over a period of 15 mins. to a solution of 2-difluoromethyl-5-hexenoyl chloride prepared as in Step E (8.760 g, 48 mM) in acetone (35 ml) at 0° C. After stirring for 0.5 hour at 0° C., the mixture is diluted with water (10 ml) and extracted with diethylether. The organic layer (100 ml) is dried over anhydrous magnesium sulfate and concentrated in vacuo and at room temperature to one fifth of its initial volume. The acylazide is fairly unstable and is directly transformed into the required methyl carbamate without further purification.

Anhydrous methanol (20 ml) is added to the ethereal solution of the acylazide and the mixture is heated at 50° C. for 15 hours. The solvent is evaporated in vacuo yielding the required methyl carbamate as a yellow oil which is purified by chromatography (medium pressure silica gel chromatography technique; ethyl acetate/cyclohexane 2:8): 400 g yield: 43%.

NMR (CDCl$_3$) 1.27–2.47 (m, 4H); 3.67 (s) and 3.50–4.28 (m) (4H); 4.73–5.22 (m); 5.45–6.12 (m) and 5.72 (td; $J_{HF}=54$ Hz, $J_{HH}=2$ Hz) (4H).

(G) Preparation of: 1,1-Difluoro 2-methoxycarbonylamino-5-pentanoic acid

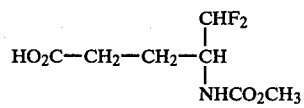

1,1-Difluoro-2-methoxycarbonylamino-4-pentene prepared as in Step F (4.00 g, 20.7 mM), dissolved in glacial acetic acid (60 ml), is added to potassium permanganate (9.80 g, 62 mM) in water (300 ml) at 0° C. After stirring for 15 hours at room temperature, the excess of potassium permanganate is destroyed with a 10% sodium bisulfite solution and the mixture saturated with sodium chloride. Extraction with diethyl ether and evaporation of the solvent in vacuo affords 1,1-difluoro-2-methoxycarbonylamino-5-pentanoic acid as a colorless oil. Crystallization from ether/petroleum ether gives 3.200 g of pure acid.

Yield 73% Mp: 77° C.

NMR (CDCl$_3$) 1.60–2.20 (m, 2H), 2.30–2.63 (m, 2H); 3.50–4.30 (m) and 3.67 (s) (4H); 5.05 (d, broad, 1H); 5.77 (td, $J_{HF}=55$ Hz, $J_{HH}=2$ Hz, 1H).

(H) Preparation of: 1,1-Difluoro-2,4-di(methoxycarbonylamino)-butane

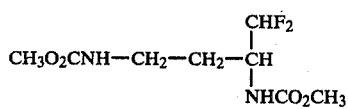

A mixture of 1,1-difluoro-2-methoxycarbonylamino-5-pentanoic acid prepared as in Step G (1.05 g, 4.97 mM), diphenylphosphoryl azide (1.370 g, mM) and triethylamine (0.505 g, 5 mM) in benzene (20 ml) is heated at reflux for 1 hour. An excess of anhydrous methanol (10 ml) is then added and refluxing continued for 17 hours. The solvent is evaporated in vacuo. The residue is dissolved in methylene chloride. The organic phase is washed three times with a 5% citric acid solution, once with water, three times with saturated sodium bicarbonate solution, and then once again with water, dried over anhydrous magnesium sulfate, filtered and evaporated in vacuo yielding a white solid. Recrystallization from ether/pentane affords 0.200 g of pure 1,1-difluoromethyl-2,4-di-(methoxycarbonylamino)-butane. Yield: 17%.

NMR (CDCl$_3$+CD$_3$OD) 1.47–2.00 (m, 2H); 2.95–3.38 (m, 2H), 3.47–4.17 (m) and 3.60 (s) (4H); 5.67 (td, $J_{HF}$=55 Hz, $J_{HH}$=2.5 Hz, 1H).

(I) Preparation of: 1,1-Difluoro-2,4-diaminobutane

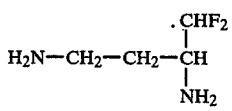

1,1-Difluoromethyl-2,4-di(methoxycarbonylamino)-butane prepared as in Step H (0.155 g, 0.64 mM) is dissolved in a mixture of glacial acetic acid (10 ml) and concentrated hydrochloric acid (30 ml). The resultant solution is heated at 110° C. yielding a yellowish solid. The solid is dissolved in water and decolourized with active charcoal. Filtration and evaporation affords 1,1-fluoro-2,4-diaminobutane, dihydrochloride as a white solid, recrystallized from ethanol/ether. 0.130 g; yield: 79%.

Mp: 190° C. (decomposition).

NMR(D$_2$O) 2.00–2.60 (m, 2H); 3.10–3.50 (m, 2H); 3.58–4.37 (m, 1H); 6.30 (td, $J_{HF}$=52 Hz, $J_{HH}$=2 Hz, 1H).

1,1-Difluoro 2,4-diaminobutane, dihydrochloride (0.985 g, 5 mM) is dissolved in water (10 ml) and the pH of the solution is adjusted to 11–12 at 0° C., with a 2 N sodium hydroxide solution. The mixture is then saturated with sodium chloride and extracted with diethyl ether (3×10 ml). The organic phase is dried over anhydrous magnesium sulfate. Filtration and evaporation of the solvent in vacuo afford the free diamine as a colorless oil.

EXAMPLE 3

1,1-Difluoro-2,4-diaminobutane

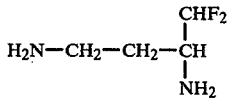

(A) Preparation of: 2-(2-Phthalimidoethyl) propanedioic acid, bis tert.-butyl ester

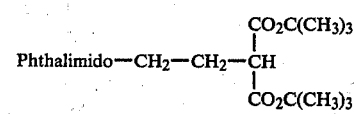

Di-t-butyl malonate (34.560 g, 160 mM), is added at room temperature, under nitrogen, to a suspension of sodium hydride (7.875 g of a 55% dispersion in oil) in anhydrous tetrahydrofuran (200 ml). After stirring for 1 hour, a solution of N-(2-bromoethyl) phthalimide (40.640 g, 160 mM) in tetrahydrofuran (100 ml) is added dropwise over a period of 20 minutes and then stirring is continued for 48 hours. The mixture is then hydrolysed and extracted with diethyl ether. The organic phase is dried over anhydrous magnesium sulfate and the solvent is evaporated in vacuo.

2-(2-Phthalimidoethyl) propanedioic acid, bis tert.-butyl ester is isolated by chromatography (medium pressure silica gel chromatography technique, ethyl acetate/cyclohexane 2:8).

NMR (CDCl$_3$) 1.40 (s, 18H); 2.22 (m, 2H); 3.17 (t; $J_{HH}$=7 Hz, 1H); 3.73 (t, $J_{HH}$=7 Hz, 2H); 7.50–7.87 (m, 4H).

(B) Preparation of: 2-Difluoromethyl-2-(2-phthalimidoethyl)-propanedioic acid, bis tert. butyl ester

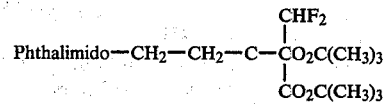

2-(2-phthalimidoethyl)-propanedioic acid, bis tert.-butyl ester prepared as in Step A (2.335 g, 6 mM) is added at room temperature under nitrogen to a suspension of sodium hydride (0.322 g of a 55% dispersion in oil) in tetrahydrofuran (15 ml). After stirring and heating at 60° C. for 6 hours, a stream of chlorodifluoromethane is bubbled through the anion solution. Stirring and heating are continued for 15 hours. The mixture is then hydrolysed and extracted twice with ether. The organic layer is dried over anhydrous magnesium sulfate and the solvent is evaporated in vacuo. The desired product is isolated by chromatography (medium pressure silica gel chromatography technique, ethy acetate/cyclohexane 2:8). Recrystallized from ether/pentane: 0.770 g (yield 30%).

Mp 107° C.

NMR (CDCl$_3$) 1.50 (s, 18H); 2.08–2.60 (m, 2H); 3.62–4.08 (m, 2H); 6.25 (t, $J_{HF}$=54 Hz, 1H); 7.47–7.85 (m, 4H).

(C) Preparation of: 2-Difluoromethyl-4-phthalimido-butanoic acid

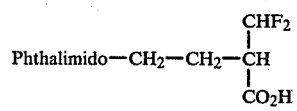

2-Difluoromethyl-2-(2-phthalimidoethyl)-propanedioic acid, bis tert.-butyl ester prepared as in Step B (0.610 g, 1.40 mM) is dissolved in trifluoroacetic acid (8 ml) at room temperature. After stirring for 1.5 hour at room temperature, the solvent is evaporated in vacuo yielding a white solid. The crude disubstituted malonic acid is dissolved in glacial acetic acid (20 ml) and the mixture is heated at 100° C. for 15 hours. The solvent is evaporated in vacuo yielding a yellowish oil. Crystallization in ether affords the required acid as a white solid (0.240 g, yield 60%). NMR (CDCl$_3$+CF$_3$CO$_2$H) 2.00–2.43 (m, 2H); 2.57–3.40 (m, 1H); 3.90 (t, J$_{HH}$=7 Hz, 2H); 6.03 (td, J$_{HF}$=55 Hz, J$_{HH}$=4 Hz, 1H); 7.58–7.95 (m, 4H).

(D) Preparation of: 1,1-Difluoro-2,4-diaminobutane

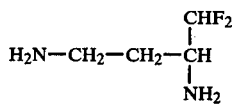

2-Difluoromethyl 4-phthalimido-butanoic acid (0.240 g, 0.85 mM) prepared as in Step C is dissolved in thionyl chloride (15 ml) and the mixture heated at reflux for 4 hours. The solvent is evaporated in vacuo leaving a yellowish oil.

Sodium azide (0.058 g, 1.05 eq) in water (0.5 ml) is added dropwise at room temperature to the crude acyl chloride (0.85 mM) dissolved in acetone. After 1 hour stirring at room temperature, the mixture is diluted with water (10 ml) and extracted with ether. The organic layer is dried over anhydrous magnesium sulfate and the solvent is evaporated in vacuo yielding a yellow oil.

NMR (CDCl$_3$) 1.83–2.37 (m, 2H); 2.47–3.30 (m, 1H); 3.50–3.93 (t, J$_{HH}$=7 Hz, 2H); 5.92 (td, J$_{HF}$=55 Hz, J$_{HH}$=4 Hz, 1H); 7.43–7.76 (m, 4H)

The crude acyl azide is dissolved in benzene (20 ml) and the mixture heated at reflux for 15 hours. The solvent is evaporated in vacuo yielding the expected isocyanate as a yellow oil.

IR (CHCl$_3$): 2250 cm$^{-1}$ (s).

NMR (CDCl$_3$) 1.67–2.27 (m, 2H); 3.40–4.13 (m, 3H); 5.73 (td, J$_{HF}$=55 Hz, J$_{HH}$=3 Hz, 1H); 7.43–7.87 (m, 4H).

The alpha-difluoromethyl isocyanate is dissolved in concentrated hydrochloric acid, and the mixture heated at 100° C. for 18 hours. The solvent is evaporated in vacuo. The residue is taken off in water. The aqueous layer is extracted four times with ether and then decolourized with active charcoal. Filtration and evaporation of the solvent affords 1,1-difluoro-2,4-diaminobutane, dihydrochloride as a white solid.

NMR (D$_2$O): 2.00–2.60 (m, 2H); 3.10–3.50 (m, 2H); 3.58–4.37 (m, 1H); 6.30 (td, J$_{HF}$=52 Hz, J$_{HH}$=2 Hz, 1H).

The free base is obtained from the dihydrochloride in the manner described in Example 2, Step I.

EXAMPLE 4

1,1-Difluoro-2,4-diaminobutane (A) Preparation of: Ethyl 4,4-difluoro-3-benzylamino-2-butenoate

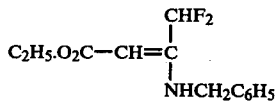

A mixture of ethyl 4,4-difluoro-3-oxo butanoate (E. T. McBee et. al, J. Amer. Chem. Soc. 75 (1953) 3152) (7.140 g 43 mM), benzylamine (4.600 g, 43 mM), p-toluenesulfonic acid (0.010 g) and benzene (60 ml) is heated at reflux for 20 hours in a flask (250 ml) fitted with a Dean Stark apparatus. The solvent is evaporated in vacuo leaving a yellow oil. Ethyl-4,4-difluoro-3-benzylamino 2-butenoate is isolated by distillation under reduced pressure: 9.200 g (yield 84%).

Bp: 100° C./0.02 mb

NMR (CDCl$_3$) 1.21 (t, J$_{HH}$=7 Hz, 3H); 4.07 (q, J$_{HH}$=7 Hz, 2H); 4.43 (AB, J$_{AB}$=16 Hz, γ$_{AB}$=15.5 Hz 2H); 4.80 (s, 1H); 5.92 (t, J$_{HF}$=53 Hz, 1H); 7.23 (s, 5H).

(B) Preparation of: Ethyl 4,4-difluoro-3-benzylamino-butanoate

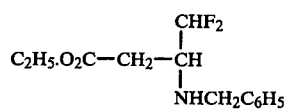

To a solution of ethyl 4,4-difluoro-3-benzylamino 2-butenoate (1.016 g, 4 mM) prepared as Step A in methanol (4 ml) at room temperature was added a trace of bromophenol blue. A 2 N hydrochloric acid-methanol solution was added until the color turned yellow. Sodium cyanohydridoborate (purified as described in R. F. Borch et al, J. Amer. Chem. Soc. 93 (1971) 2897) (0.390 g, 6 mM) was added with stirring.

The hydrochloric acid-methanol solution was then added dropwise to maintain the yellow color. Stirring was continued for 7 hours at room temperature. The solution is poured into 0.1 N sodium hydroxide (5 ml) and the pH adjusted to 10. The aqueous layer is saturated with sodium chloride and extracted three times with ether. The combined extracts are dried over anhydrous magnesium sulfate, and the solvent is evaporated in vacuo yielding a yellow oil. Ethyl 4,4-difluoro-3-benzylamino-butanoate is isolated by chromatography (medium pressure silica gel chromatography technique, ethyl acetate cyclohexane 2:8): 0.765 g (yield 75%).

NMR (CCl$_4$) 1.20 (t, J$_{HH}$=7 Hz, 3H); 2.30–2.55 (m, 2H); 2.83–3.57 (m, 1H); 3.80 (s, 2H); 4.03 (q, J$_{HH}$=7 Hz, 2H); 5.68 (td, J$_{HF}$=56 Hz, J$_{HH}$=3.5 Hz, 1H); 7.13 (s, 5H).

(C) Preparation of: 4,4-Difluoro-3-benzylamino-butanol

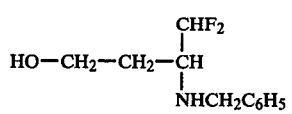

A solution of ethyl 4,4-difluoro 3-benzylamino butanoate (1.024 g, 4 mM) prepared as in Step B in anhydrous diethyl ether (10 ml) is added dropwise at room temperature to a mixture of lithium aluminium hydride (0.152 g, 4 mM) in diethyl ether (40 ml) over a period of 1 hour. Stirring is continued for 22 hours. The mixture is then hydrolysed by the addition of water (0.152 ml), a 15% solution of sodium hydroxide in water (0.152 ml) and again water (0.152 ml). The resultant mixture is stirred for 1 hour. Anhydrous magnesium sulfate (0.200 g) is added. Filtration and distillation of the solvent in vacuo yield the 4,4-difluoro-3-benzylamino-butanol as a colorless oil: 0.790 g (yield 92%).

NMR (CDCl$_3$): 1.47–1.93 (m, 2H); 2.63–3.58 (m, 2H); 3.70 (t, J$_{HH}$=5.5 Hz) and 3.87 (s, broad) (4H); 5.70 (td, J$_{HF}$=56 Hz, J$_{HH}$=3 Hz, 1H); 7.23 (s, 5H).

(D) Preparation of: N-(4,4-difluoro-3-benzylamino-butyl)-phthalimide

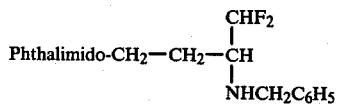

A solution of diethyl azodicarboxylate (0.639 g, 3.65 mM), in anhydrous tetrahydrofuran (5 ml) is added, dropwise, over a period of 0.5 hours, at room temperature to a mixture of 4,4-difluoro-3-benzylamino-butanol (0.790 g, 3.65 mM) prepared as in Step C, triphenylphosphine (0.962 g, 3.65 mM), and phthalimide (0.540 g, 3.65 mM) in tetrahydrofuran (20 ml). After stirring for 2.5 hours at room temperature, the solvent is evaporated in vacuo. The residue is taken off in benzene and the solution filtered. The solid is washed three time with benzene. The filtrate is evaporated to dryness; the residue is taken off in diethyl ether. Filtration and evaporation of the solvent in vacuo yields a yellow oil. The expected phthalimide is isolated by column chromatography (medium pressure silica gel chromatography technique, ethyl acetate/cyclohexane 2:8): 0.800 g (yield 65%).

NMR (CDCl$_3$) 1.33–2.13 (m, 3H); 2.50–3.27 (m, 1H); 3.78 (t, J$_{HH}$=7 Hz) and 3.83 (s, broad) (4H); 5.68 (td, J$_{HF}$=56 Hz, J$_{HH}$=3 Hz, 1H); 7.15 (s, broad, 5H); 7.40–7.80 (m, 4H).

(E) Preparation of: 1,1-Difluoro-2-benzylamino-4-amino-butane, dihydrochloride

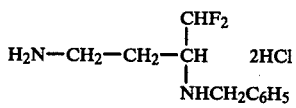

A solution of N-(4,4-difluoro-3-benzylaminobutyl) phthalimide (0.585 g, 1.72 mM) prepared as in Step D in concentrated hydrochloric acid (50 ml) is heated at 110° C. for 15 hours. The solvent is evaporated in vacuo, and the residue is taken up in cold water (50 ml). The aqueous phase is filtered and concentrated in vacuo, washed three times with diethyl ether, and then evaporated to dryness. The oily residue is triturated several times with isopropanol. The solvent is removed in vacuo yielding a white foam: 0.490 g (quantitative yield) of the required compound.

The free 1,1-difluoro-2-benzylamino-4-amino-butane is isolated by extraction with ether of the aqueous phase (saturated with sodium chloride) at pH about 10.

1,1-difluoro-2-benzylamino-4-amino-butane.

NMR (CDCl$_3$) 1.10–1.87 (m, 5H); 2.40–3.17 (m,3H); 3.80 (s, broad, 2H); 5.63 (td, J$_{HF}$=56 Hz, J$_{HH}$=3.5 Hz, 1H); 7.17 (s, 5H).

(F) Preparation of: 1,1-Difluoro-1,4-diaminobutane

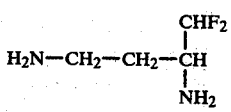

A mixture of 1,1 difluoro-2-benzylamino-4-aminobutane, dihydrochloride (0.490 g, 1.70 mM) prepared as in Step E, 5% palladium on charcoal (type H, 0.120 g), and glacial acetic acid (30 ml) is shaken, under hydrogen (60 psi) in a Parr hydrogenator for 40 hours at room temperature. The catalyst is then removed by filtration, washed three times with water, and the filtrate evaporated to dryness in vacuo. The expected diamine dihydrochloride is isolated by crystallization of the oily residue in ethanol/ether: 0.220 g (yield 67%).

Mp: 190° C. (decomposition)

NMR (D$_2$O) 2.00–2.60 (m, 2H); 3.10–3.50 (m, 2H); 3.58–4.37 (m, 1H); 6.30 (td, J$_{HF}$=52 Hz, J$_{HH}$=52 Hz, 1H).

The free base is obtained from the dihydrochloride in the manner described in Example 2, Step I.

EXAMPLE 5

1,1-Difluoro-2Amino-4-Benzylamino-Butane

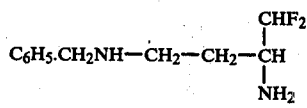

(A) Preparation of: Ethyl 4,4-difluoro 3-amino-2-butenoate

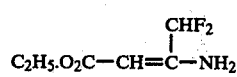

Ammonium acetate (62 g, 805 mM) is added at room temperature to a solution of ethyl 4,4-difluoro acetoacetate (7.400 g, 44.5 mM) in anhydrous methanol (120 ml). Stirring is continued at room temperature for 40 hours; the mixture is then poured into 5% sodium bicarbonate solution (200 ml), and extracted with ether (2×150 ml). The organic layer is dried over anhydrous magnesium sulfate. The solvent is evaporated in vacuo, yielding the expected compound as a yellowish oil. 4.700 g (yield 65%). IR (CHCl$_3$): 3500, 1680, 1640 cm$^{-1}$.

NMR (CDCl$_3$) 1.27 (t,J$_{HH}$=7 Hz, 3H); 4.14 (q, J$_{HH}$=7 Hz, 2H); 4.83 (s, broad, 1H); 5.95 (t, J$_{HF}$=55 Hz, 1H).

(B) Preparation of: Ethyl 4,4-difluoro-3-amino-butanoate

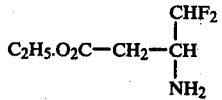

To a solution of ethyl 4,4-difluoro 3-amino 2-butenoate prepared as in Step B (3.10 g, 18.8 mM) in methanol (30 ml) at room temperature was added a trace of bromophenol blue. A 2 N HCl-methanol solution was added until the color turned yellow (pH=3.0–3.5).

Sodium cyanohydridoborate (1.830 g, 28.2 mM) was added with stirring. The 2 N HCl-methanol solution was then added dropwise to maintain the pH around 3.0–3.5. Stirring was continued for 3 hours at room temperature. The solution is poured into 0.1 N sodium hydroxide (15 ml). The aqueous layer is saturated with sodium chloride and extracted with ether (3×20 ml). The combined extracts are dried over anhydrous magnesium sulfate, and the solvent is evaporated in vacuo yielding the expected amino-ester as yellow oil. 2.880 g (yield 70%).

NMR (CDCl₃) 1.27 (t, $J_{HH}$=7 Hz, 3H); 2.13–2.87 (m, 2H); 3.00–3.70 (m, 1H); 4.16 (q, $J_{HH}$=7 Hz, 2H); 5.72 (td, $J_{HF}$=56 Hz, $J_{HH}$=4 Hz, 1H).

(C) Preparation of: 4,4-Difluoro-3-amino-butanoic acid, hydrochloride

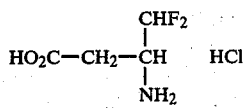

Ethyl 4,4-difluoro-3-amino-butanoate prepared as in Step B (3.340 g, 20 mM) is dissolved in 1 M HCl (20 ml) and the mixture heated at 100° C. for 3 hours. The solvent is evaporated in vacuo. The oily residue is crystallized from ethanol/ether; 2.800 g of 4,4-difluoro-3-amino-butanoic acid, hydrochloride (yield 80%). Mp: 150° C.

NMR (D₂O) 2.80–3.10 (m, 2H); 3.75–4.60 (m, 1H); 6.30 (td, $J_{HF}$=53 Hz, $J_{HH}$=2 Hz, 1H).

(D) Preparation of: 4,4-Difluoro-3-tert.-butoxycarbonylamino-butanoic acid

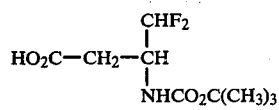

A mixture of 4,4-difluoro-3-amino-butanoic acid, hydrochloride prepared as in Step C (0.702 g, 4 mM), ditertiobutyl dicarbonate (0.916 g, 4.2 mM), sodium bicarbonate (0.336 g, 4 mM) in tetrahydrofuran and water (6 ml of a 1:1 mixture) is heated at reflux for 48 hours. The resulting solution is saturated with sodium chloride and extracted three times with chloroform. The organic phase is dried over anhydrous magnesium sulfate, and the solvent evaporated in vacuo yielding a colorless oil.

NMR (CDCl₃) 1.45 (s, 9H); 2.50–2.80 (m, 2H); 3.74–4.67 (m, 1H); 5.84 (td, $J_{HF}$=56 Hz, $J_{HH}$=3 Hz, 1H).

(E) Preparation of: 4,4-Difluoro-n-benzyl 3-tert.-butoxycarbonylaminobutanamide

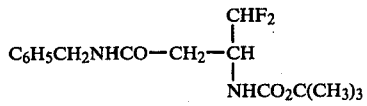

A solution of benzylamine (0.214 g, 2 mM) in acetonitrile (5 ml) is added, at 0° C., to a mixture of 4,4-difluoro-3-tert.-butoxycarbonylamino-butanoic acid (0.478 g, 2 mM) prepared as in Step D and N,N¹-dicyclohexylcarbodiimide (0.412 g, 2 mM) in acetonitrile (15 ml). After stirring for 24 hours at room temperature, the precipitate is filtered and thoroughly rinsed with acetonitrile. The solvent is evaporated in vacuo yielding a yellowish oil. The expected amide is isolated by column chromatography (medium pressure silica gel chromatography technique, ethyl acetate/cyclohexane 4:6).

(F) Preparation of: 1,1-Difluoro-2-amino-4-benzylamino-butane

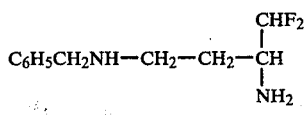

To a solution of borane (H. C. Brown, P. Heim, J. Amer. Chem. Soc. 86, 3566 (1964) in tetrahydrofuran (1 M, 7 ml, 7 mM), under nitrogen, is added, at 0° C., a solution of 4,4-difluoro-N-benzyl-3-tert.-butoxycarbonylamino-butanamide (0.984 g, 3 mM) prepared as in Step E in tetrahydrofuran (15 ml) over a period of 15 min. The solution is then heated at reflux temperature for 4 hours. After cooling to room temperature, 6 M hydrochloric acid (5 ml) is added. The solvent is removed in vacuo. The residue is passed on an ion exchange column (Dowex 50, H+) (elution with water (500 ml) and then diluted hydrochloric acid (0.1 M to 3 M); by collecting the fractions giving a positive ninhydrine test the expected diamine dihydrochloride is isolated as a white solid, recrystallized from ethanol/ether.

1,1-Difluoro 2-amino 4-benzylamino-butane, dihydrochloride (0.861 g, 3 mM) is dissolved in water (8 ml) and the pH of the solution is adjusted to 11-12 at 0° C. with a 2 N sodium hydroxide solution. The mixture is then saturated with sodium chloride and extracted with ether (3×10 ml). The organic phase is dried over anhydrous magnesium sulfate. Filtration and evaporation of the solvent in vacuo afford the expected free diamine, as a colorless oil.

In the following Examples relating to pharmaceutical compositions, the term "active compound" is used to indicate the compound 1-fluoro-2,4-diaminobutane. This compound may be replaced in these compositions by any other compound of the invention, for example by 1,1-difluoro-2,4-diaminobutane. Adjustments in the amount of medicament may be necessary or desirable depending upon the degree of activity of the medicament as is well known in the art.

EXAMPLE 6

An illustrative composition for hard gelatin capsules is as follows:
(a) active compound: 20 mg,
(b) talc: 5 mg,
(c) lactose: 90 mg.

The formulaton is prepared by passing the dry powders of (a) and (b) through a fine mesh screen and mixing them well. The powder is then filled into hard gelatine capsules at a net fill of 115 mg per capsule.

EXAMPLE 7

An illustrative composition for tablets is as follows:
(a) active compound: 20 mg,
(b) starch: 43 mg,
(c) lactose: 45 mg,
(d) magnesium stearate: 2 mg.

The granulation obtained upon mixing the lactose with the compound (a) and the part of the starch and granulated with starch paste is dried, screened, and mixed with the magnesium stearate. The mixture is compressed into tables weighing 110 mg each.

EXAMPLE 8

An illustrative composition for an injectable suspension is the following 1 ml ampul for an intramuscular injection:

|  | Weight percent |
| --- | --- |
| (a) active compound | 1.0 |
| (b) polyvinylpyrrolidone | 0.5 |
| (c) lecithin | 0.25 |
| (d) water for injection to make | 100.0 |

The materials (a)–(d) are mixed, homogenized and filled into 1 ml ampuls which are sealed and autoclaved 20 minutes at 121° C. Each ampul contains 10 mg per ml of novel compound (a).

EXAMPLE 9

|  | mg/suppository |
| --- | --- |
| Active compound | 50 |
| Oil of Theobroma | 950 |

The medicament is powdered and passed through a B.S. No. 100 Sieve and triturated with molten oil of Theobroma at 45° C. to form a smooth suspension. The mixture is well stirred and poured into moulds each of nominal 1 G capacity, to produce suppositories.

EXAMPLE 10

The ability of the compounds of Formula I to inhibit GABA-T enzyme and to increase GABA concentration in the brain can be demonstrated in the following test procedures in mice.

A group of 10 male albino CDI mice from Charles Riner, France, is given an i.p. injection of the test compound in aqueous solution daily for four consecutive days. Half of the animals are killed by decapitation 24 hours after the last dose of the test compound. The other half of the animals are observed for up to 12 days for toxicity (as indicated by weight loss and deaths). Control animals receive an injection of the vehicle only.

The brains are removed from the dead mice and are divided into two portions by sagittal section. One half is used for the measurement of GABA-T activity while the other half is used for measuring GABA content. The GABA-T activity is measured using known methods as described by M. Jung et al., *J. Neurochem.*, 28, 717 (1977) and 29, 797 (1977). GABA content is measured by perchloric acid or trichloroacetic acid extracts using an amino acid analyzer equiped with a fluorescene detector.

When tested as described above, 1-fluoro-2,4-diaminobutane (MFDB) and 1,1-difluoro-2,4-diaminobutane (DFDB) gave the results set forth in Table I below:

TABLE 1

| Compound | Daily Dose (mg/kg) | GABA-T Inhibition (%) | GABA-T Elevation (%) | Weight Loss (%) | Morality (After treatment) |
| --- | --- | --- | --- | --- | --- |
| DFDB | 2 | 69.5 | — | 0 | 0/5 |
|  | 5 | 71.4 | 200 | 0 | 0/5 |
|  | 10 | 81 | 275 | −25 | 2/5 by day 8 |
|  | 20 | 96.7 | 465 | −30 | 5/5 by day 6 |
| MFDB | 5 | 39.7 | 190 | 0 | 0/5 |
|  | 10 | 49.8 | 200 | 0 | 0/5 |
|  | 25 | 74 | 470 | −20 | 2/5 on day 12 |
|  | 50 | 79 | 465 | −35 | 3/5 on day 8 |

EXAMPLE 11

The ability of the compounds of Formula I to protect mice against clonic seizures induced by an i.v. challenge of (+)-bicuculline is demonstrated by the procedure described by Buckett et al., *Br.J.Pharmacol.*, 68, 177 (1980) and *Journal of Pharmacological Methods*, 5, 35 (1981).

When tested using the procedure above-described, 1-fluoro-2,4-diaminobutane (MFDB) and 1,1-difluoro-2,4-diaminobutane (DFDB) gave the following results:

TABLE 2

| Compound | Dose, i.p. (mg/kg) | % of Animals Blocked | ED$_{50}$ (mg/kg) |
| --- | --- | --- | --- |
| MFDB | 100 | 60 |  |
|  | 84 | 60 |  |
|  | 68 | 55 |  |
|  | 59 | 50 | 65 |
|  | 51 | 40 |  |
|  | 42 | 20 |  |
| DFDB | 8 | 95 |  |
|  | 6 | 90 | 4.2 |
|  | 4 | 45 |  |
|  | 3 | 20 |  |

What is claimed is:

1. A compound of the formula:

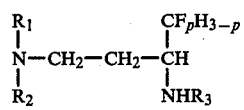

wherein:
R$_1$ is hydrogen, C$_1$–C$_6$alkyl or phenyl-(C$_1$–C$_4$alkyl);
R$_2$ is hydrogen, C$_1$–C$_6$alkyl, phenyl-(C$_1$–C$_4$alkyl), or R$_4$, where R$_4$ is as defined below;
R$_3$ is hydrogen or, except when R$_2$ is R$_4$, R$_4$, where R$_4$ is as defined below;
each R$_4$, independently, is C$_2$–C$_5$alkylcarbonyl, phenylcarbonyl, phenyl-(C$_1$–C$_4$alkyl)carbonyl, or an aminocarboxylic acid residue derived by removal of an hydroxy group from the carboxy moiety of glycine or an L-aminocarboxylic acid of the formula HOCOCH(R$_9$)NH$_2$ or HO—CO(CH$_2$)$_n$CH(NH$_2$)CO$_2$H wherein R$_9$ is C$_1$–C$_4$alkyl, aminopropyl, aminobutyl, benzyl, or p-hydroxybenzyl and n is 1 or 2; and
p is 1 or 2,
or a pharmaceutically acceptable acid addition salt thereof.

2. A compound as defined in claim 1 wherein both R$_1$ and R$_2$ are hydrogen.

3. The compound as defined in claim 2 which is 1-fluoro-2,4-diaminobutane.

4. The compound as defined in claim 2 which is 1,1-difluoro-2,4-diaminobutane.

5. A compound as defined in claim 2 wherein $R_3$ is $R_4$.

6. A compound as defined in claim 1 wherein $R_3$ is hydrogen.

7. A compound as defined in claim 6 wherein $R_1$ is hydrogen and $R_2$ is ($C_1$–$C_4$ alkyl) or phenyl-($C_1$–$C_4$ alkyl).

8. The compound as defined in claim 7 which is 1,1-difluoro-2-amino-4-benzylaminobutane.

9. A compound as defined in claim 6 wherein $R_1$ is hydrogen and $R_2$ is $R_4$.

10. A compound as defined in claim 1, 2, 5, 6, 7, or 9 wherein p is 1.

11. A compound as defined in claim 1, 2, 5, 6, 7, or 9 wherein p is 2.

12. A pharmaceutical composition for inhibiting GABA-T comprising a GABA-T inhibiting effective amount of a compound as defined in claim 1 and a pharmaceutically acceptable carrier.

13. A pharmaceutical composition as defined in claim 12 wherein the compound is 1-fluoro-2,4-diaminobutane, 1,1-difluoro-2,4-diaminobutane, or 1,1-difluoro-2-amino-4-benzylaminobutane, or a pharmaceutically acceptable acid addition salt thereof.

* * * * *